US012582554B2

(12) United States Patent
Gustavsson

(10) Patent No.: US 12,582,554 B2
(45) Date of Patent: Mar. 24, 2026

(54) WELDING PROTECTION DEVICE WITH HAPTIC SENSING

(71) Applicant: 3M INNOVATIVE PROPERTIES COMPANY, St. Paul, MN (US)

(72) Inventor: Stefan G. Gustavsson, Falun (SE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 18/693,255

(22) PCT Filed: Sep. 15, 2022

(86) PCT No.: PCT/IB2022/058712
§ 371 (c)(1),
(2) Date: Mar. 19, 2024

(87) PCT Pub. No.: WO2023/047254
PCT Pub. Date: Mar. 30, 2023

(65) Prior Publication Data
US 2024/0285440 A1      Aug. 29, 2024

Related U.S. Application Data

(60) Provisional application No. 63/261,444, filed on Sep. 21, 2021.

(51) Int. Cl.
*A61F 9/06* (2006.01)
*F16P 1/06* (2006.01)

(52) U.S. Cl.
CPC ............... *A61F 9/067* (2013.01); *A61F 9/06* (2013.01); *A61F 9/065* (2013.01)

(58) Field of Classification Search
CPC ............. A61F 9/067; A61F 9/06; A61F 9/065
See application file for complete search history.

(56) References Cited

U.S. PATENT DOCUMENTS

| | | | | | |
|---|---|---|---|---|---|
| 4,498,202 | A | * | 2/1985 | Yamamoto | ............... A42B 3/28 |
| | | | | | 2/424 |
| 4,679,255 | A | * | 7/1987 | Kuhlman | ................ A61F 9/061 |
| | | | | | 2/8.3 |
| 5,208,688 | A | | 5/1993 | Fergason et al. | |
| 5,248,880 | A | | 9/1993 | Fergason et al. | |
| 5,327,588 | A | * | 7/1994 | Garneau | .............. A42B 3/0493 |
| | | | | | 2/209.13 |

(Continued)

FOREIGN PATENT DOCUMENTS

| | | | |
|---|---|---|---|
| EP | 2275061 | A1 | 1/2011 |
| KR | 101131475 | B1 | 3/2012 |

(Continued)

OTHER PUBLICATIONS

International Search report for PCT International Application No. PCT/IB2022/058712, mailed on Jan. 10, 2023, 5 pages.

*Primary Examiner* — Robert H Muromoto, Jr.

(57) ABSTRACT

A welding protection device that includes a shield body, an automatic darkening filter insertable in the shield body, and a haptic sensing unit to sense a touch pattern occurring on the shield body or automatic darkening filter assembly. Upon sensing of a touch pattern, a user definable command is executed that can place the welding protection device in a specific operational state.

16 Claims, 5 Drawing Sheets

(56)  References Cited

U.S. PATENT DOCUMENTS

| | | | | |
|---|---|---|---|---|
| 5,377,032 | A | * | 12/1994 | Fergason ................ A61F 9/067 |
| | | | | 2/8.8 |
| 5,510,961 | A | * | 4/1996 | Peng ...................... A42B 1/242 |
| | | | | D2/866 |
| 5,751,258 | A | * | 5/1998 | Fergason ................ A61F 9/067 |
| | | | | 349/8 |
| 5,896,579 | A | * | 4/1999 | Johnson .................. A61F 9/068 |
| | | | | 2/7 |
| 6,070,264 | A | * | 6/2000 | Hamilton ............... A61F 9/067 |
| | | | | 2/8.8 |
| 6,614,409 | B1 | * | 9/2003 | Bae ........................ A61F 9/065 |
| | | | | 2/8.7 |
| 6,881,939 | B1 | | 4/2005 | Hamilton et al. |
| 7,008,055 | B2 | | 3/2006 | Mclear et al. |
| 7,477,330 | B2 | | 1/2009 | Magnusson et al. |
| 8,042,958 | B2 | | 10/2011 | Sundell |
| 8,089,424 | B2 | * | 1/2012 | Huh ....................... A61F 9/067 |
| | | | | 349/13 |
| 8,340,725 | B2 | * | 12/2012 | Park ...................... G06F 1/1643 |
| | | | | 455/566 |
| 8,955,162 | B2 | * | 2/2015 | Huh ....................... A61F 9/067 |
| | | | | 2/8.8 |
| 8,959,662 | B2 | | 2/2015 | Huh |
| 8,990,963 | B2 | | 3/2015 | Matthews et al. |
| 9,009,862 | B2 | | 4/2015 | Huh |
| 9,889,045 | B2 | | 2/2018 | Matthews et al. |
| 9,937,578 | B2 | * | 4/2018 | Becker .................. G06T 19/006 |
| 11,337,483 | B2 | * | 5/2022 | Segura ................. B23K 37/006 |
| 2010/0090997 | A1 | * | 4/2010 | Huh ........................ A61F 9/067 |
| | | | | 345/207 |
| 2011/0010815 | A1 | * | 1/2011 | Huh ........................ A61F 9/067 |
| | | | | 2/8.8 |
| 2015/0375327 | A1 | * | 12/2015 | Becker ..................... G06T 1/00 |
| | | | | 219/130.01 |
| 2017/0143548 | A1 | | 5/2017 | Lee |
| 2020/0085132 | A1 | * | 3/2020 | Segura .................. A42B 3/225 |
| 2023/0410808 | A1 | * | 12/2023 | Kurzhals .............. A61F 11/145 |
| 2023/0414977 | A1 | * | 12/2023 | Thompson ............. A62B 18/04 |

FOREIGN PATENT DOCUMENTS

| | | | |
|---|---|---|---|
| KR | 101240048 | B1 | 3/2013 |
| KR | 101376630 | B1 | 3/2014 |
| KR | 101440263 | B1 | 9/2014 |
| WO | 2020061017 | A1 | 3/2020 |

* cited by examiner

WELDING PROTECTION DEVICE WITH HAPTIC SENSING

FIELD

The present technology is generally related to welding protection devices, and in particular to a welding protection device having a haptic sensing unit.

BACKGROUND

Welding protection devices such as welding helmets are typically used to protect welders from harmful irradiation emitted from the welding arc and from splashes, sparks and particles that may be ejected from a welding area. Welding helmets can be suspended on the head of a wearer, so that the wearer has both hands available for welding and handling of workpieces.

Some welding helmets are furnished with an automatic darkening filter. An automatic darkening filter commonly has a switchable filter that automatically changes from a light-state to a dark-state in response to incident light generated by the welding arc. Thus, upon ignition of the welding arc the switchable filter automatically changes to the dark-state and protects the welder's eyes and face from the irradiation emitted from welding arc. Once the welding is interrupted or ended the switchable filter automatically changes to the light-state so that the user can see through the filter at normal light conditions. Automatic darkening filters and related apparatus are described in, for example, U.S. Pat. No. 5,208,688 to Fergason et al., U.S. Pat. No. 5,248,880 to Fergason, U.S. Pat. No. 6,070,264 to Hamilton et al., U.S. Pat. No. 6,881,939 to Hamilton and Scott, U.S. Pat. No. 7,008,055 to McLear and Gerfin, and U.S. Pat. No. 8,042,958 to Sundell.

However, there are additional operations that a welder may need to accomplish that necessitate the need to change the function(s) and/or operational state(s) of the welding helmet.

SUMMARY

This disclosure generally relates to welding protection devices, and in particular to welding protection devices that including haptic sensing capabilities. In one embodiment, a welding protection device comprises a shield body, an automatic darkening filter assembly insertable within the shield body, and a haptic sensing unit to sense a touch pattern occurring on at least a first portion of the shield body or automatic darkening filter assembly.

In one aspect of the embodiment, the haptic sensing unit comprises at least one haptic sensor.

In one aspect of the embodiment the at least one haptic sensor comprises at least one of an accelerometer, a transducer, and a touch sensor.

In one aspect of the embodiment, the haptic sensor unit is programmed to execute a user-definable command.

In another aspect of the embodiment, the user definable command includes one or more of the following commands: grinding mode on/off, locked dark state on/off, Feature on/off; Accessory (on/off/control), shade level higher/lower, sensitivity level higher/lower, and predefined user-mode toggle.

In one aspect of the embodiment, the haptic sensor unit comprises a plurality of haptic sensors, wherein each sensor is disposed in a different portion of the welding protection device.

In one aspect of the embodiment, a first sensing unit comprises a first haptic sensor that senses a touch pattern performed on the front of the welding protection device, and a second haptic sensor that senses a touch pattern performed on the lateral side of the welding protection device. The touch pattern may comprise a single touch or a multiple touch.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1A:
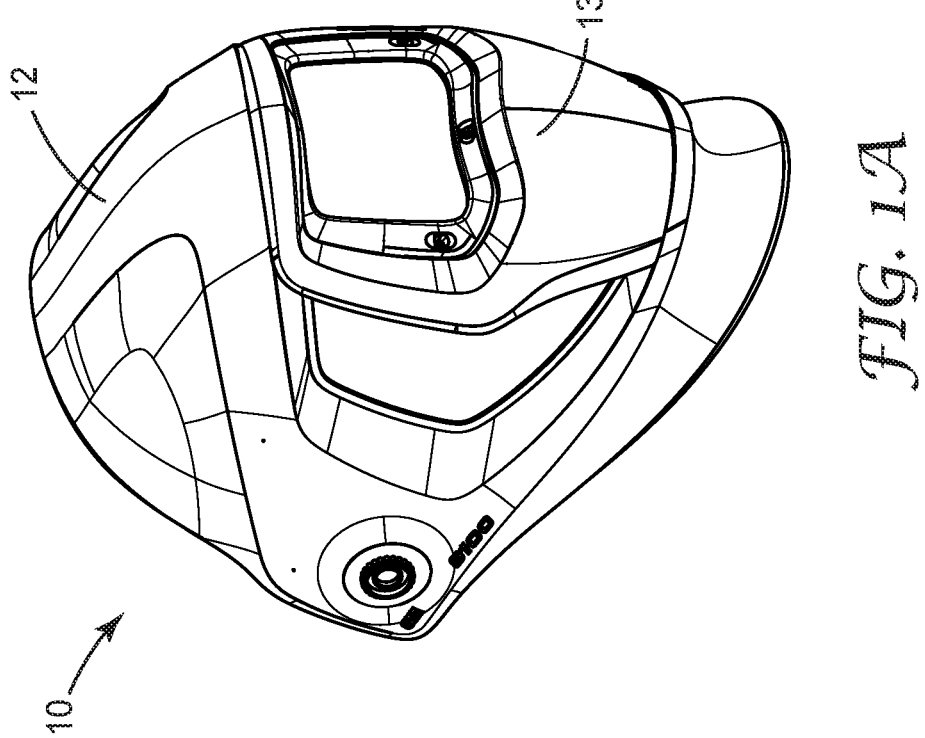
FIGS. 1A and 1B are isometric and partially exploded views of an exemplary welding protection device in accordance with embodiments of the present invention.

The present disclosure is drawn to a welding protection device, for example, a welding helmet, with haptic sensing capabilities. In particular, the welding protection device comprises a haptic sensing unit that is configured to sense touch patterns, be it a single touch, a multiple touch, a series of single/multiple touches, or a heavy or light touch, that allow a user wearing the welding protection device to change operational states and/or access one or more features of the welding protection device in a straightforward and rapid manner.

The type of quick access provided by embodiments of the present invention can be extremely convenient and/or important for the user, especially in some welding environments. These environments may make finding and actuating a conventional button, dial, switch or other mechanical actuation device cumbersome or difficult, and may require precision manipulation by the user (and may even necessitate removing equipment (e.g., removing protective gloves)). By implementing haptic sensing locations on one or more parts of the welding protection device, the requirement for such precision is reduced and the system controllability can be improved.

For example, in conventional welding protection devices, entering a particular mode, such as a grinding mode, requires accessing and manually activating an external button on the helmet or accessing the user interface on the ADF inside the helmet. This conventional approach can complicate helmet design and safety. In addition, accessing such a grinding mode activation button may be difficult in certain welding environments.

With embodiments of the present invention, a welder can instead tap anywhere on the helmet to switch to/from grind-mode.

Before describing in detail exemplary embodiments that are in accordance with the disclosure, it is noted that components have been represented where appropriate by conventional symbols in drawings, showing only those specific details that are pertinent to understanding the embodiments of the disclosure so as not to obscure the disclosure with details that will be readily apparent to those of ordinary skill in the art having the benefit of the description herein.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Referring now to the drawing figures in which like reference designations refer to like elements, an embodiment of a welding protection device constructed in accordance with the principles of the present disclosure is shown in the figures and generally designated as "10." In this example, the welding protection device comprises a welding helmet. In this regard, the welding helmet may comprise a hard or soft shield or mask, preferably that incorporates an automatic darkening filter.

Figure 1B:
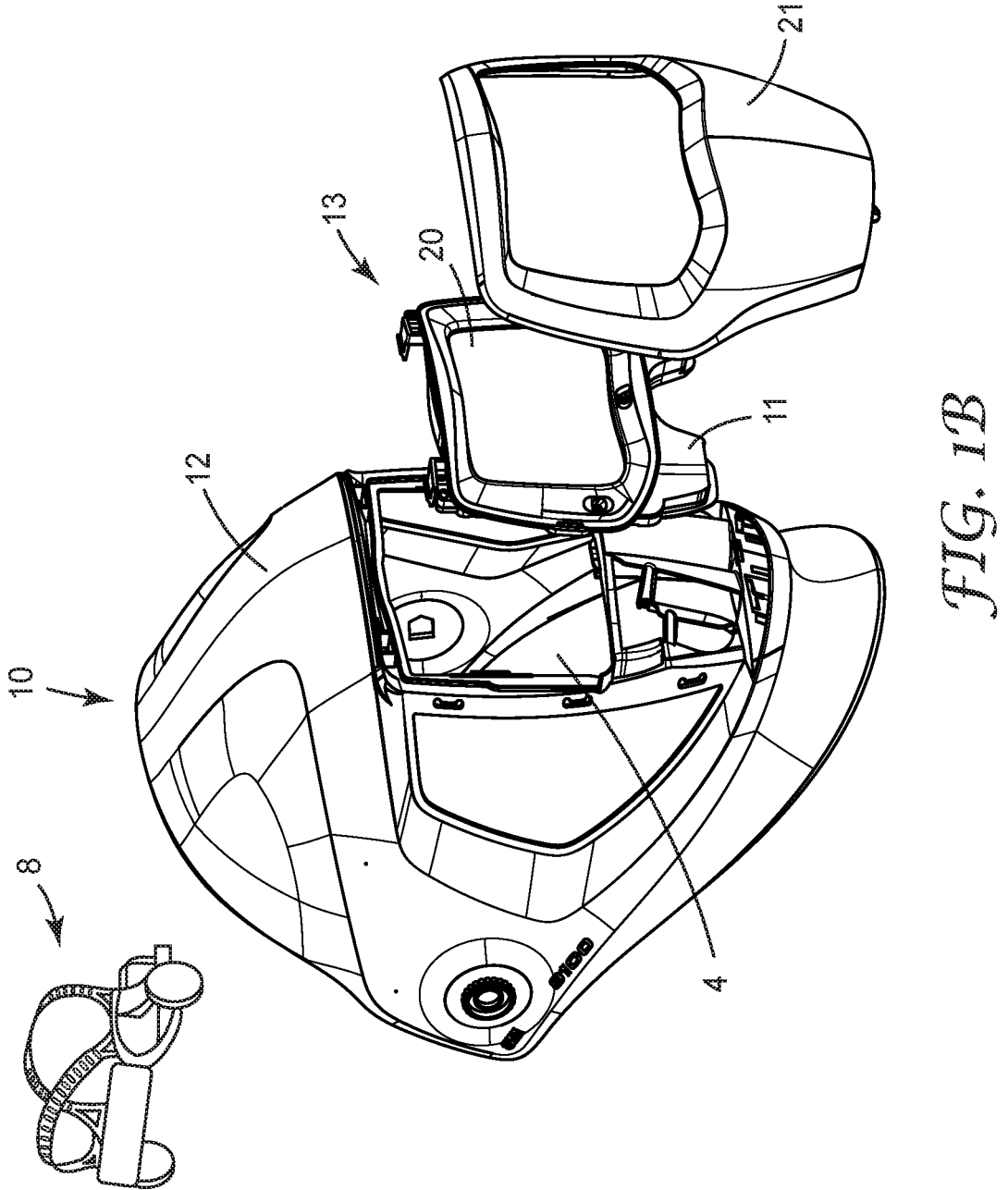

The welding protection device or welding helmet 10 shown in FIGS. 1A and 1B generally includes a shield body or portion 12 for protecting a welder's face (and other head portions) from radiation, dust and splashes of hot materials as these may occur during welding. The welding helmet 10 further has an automatic darkening filter (ADF) assembly 13 that includes a shutter/ADF 20 through which the welder can observe the welding arc during welding. Preferably, ADF assembly 13 is positioned in shield body 12 so that the shutter portion is directly in front of the wearer's eyes when the welding protection device 10 is worn by the user. As will be apparent to one of skill in the art given the present description, embodiments of the invention are not limited to the specific design of the helmet shown in FIGS. 1A and 1B, as the haptic sensing unit described herein can be incorporated into alternative welding helmet configurations.

In one embodiment, as explained in more detail herein, the automatic darkening can be based on two liquid crystal cells by which the ADF assembly 13 is electrically switchable between a light-state and a dark-state. When switched in the dark-state, the ADF assembly's shutter portion 20 blocks a significant amount of light from being transmitted therethrough. This allows a user to observe a welding arc by seeing through the ADF assembly 13 without risking eye exposure to harmful light radiation from the welding arc. In the light-state, the ADF assembly 13 permits a significant amount of light to be transmitted therethrough. Thus, the ADF assembly 13 in the light-state allows the user to see under ambient light conditions (in the absence of the welding arc). In this context, "light" means electromagnetic radiation of a wavelength that might be capable of damaging the eyes of a user, or of causing perceived discomfort to the user. In this context, such light includes at least visible light, and may also include infrared and/or ultraviolet radiation, whether or not such radiation is perceptible to the user. In this context, "high intensity" light means light that is present at such intensity (e.g., such as that emitted by a device such as an arc welder) such that it might be capable of damaging the eyes of a user, or of causing perceived discomfort to the user.

In other embodiments, ADF assembly 13 can comprise a combination of layers of liquid crystals and polarizing filters, as described in, for example, U.S. Pat. No. 7,477,330 to Magnusson et al. In other embodiments, ADF assembly 13 may be constructed using electrochromic materials.

Automatic darkening filter assembly 13 can be used in connection with industrial operations, for example welding (e.g., arc welding, torch welding, acetylene welding), cutting (e.g., laser cutting, acetylene cutting), brazing, soldering and many others.

According to one embodiment of the present invention, in addition to the light-state (non-welding) and dark-state (welding) modes, the welding protection device or welding helmet 10 is further configured to enter one or more different functional states, such as a grind or grinding mode, whereby a user can perform a grinding operation which does not require significant blockage of light, but that still requires protection against splatter and high speed particles. In the grinding mode, the ADF assembly 13 can be locked in the light-state or at least one intermediate-state (allowing an amount of light between the light-state and the dark-state) when a grinding operation is being performed by the user. In addition, the dark state can be turned off (and remain locked off) while engaged in the grinding mode. In this example, the user can access the grinding mode via a touch pattern applied to a portion of the welding helmet. In this aspect, a haptic sensing unit 11 can be mounted to a portion of the helmet device 10 to enable haptic sensing capabilities.

The amount of incident light transmitted by ADF assembly 13 in the various states can be characterized in various ways. One way commonly used in the art is the visible light transmission of the shutter. In various embodiments, ADF assembly 13 is configured so as to exhibit a visible light transmission of less than about 0.5%, less than about 0.1%, or less than about 0.05%, when in a dark state; and, to exhibit a visible light transmission of greater than about 10%, greater than about 20%, or greater than about 50%, when in a light state. In various embodiments the visible light transmission of ADF assembly 13 when in an intermediate state may be less than about 10%, less than about 5%, or less than about 2%, and may be greater than about 0.5%, greater than about 1%, or greater than about 1.5%. Other ranges are possible. As indicated above, regardless of the ranges chosen, for a given ADF assembly 13, the visible light transmission of the shutter portion in the intermediate state will always be higher than that of the shutter in the dark state and lower than that of the shutter in the light state.

Performance of ADF assembly 13 may also be characterized by the shade level or "Shade Number" which is also commonly known in the art. Thus, in various embodiments ADF assembly 13 may exhibit a Shade Number of greater than about 8, greater than about 10, or greater than about 12, when in a dark state; and may exhibit a Shade Number of less than about 5, less than about 4, or less than about 3, when in a light state. In various embodiments the Shade Number of ADF assembly 13 when in an intermediate state may be less than about 8, less than about 7 or less than about 6, and may be greater than about 3, greater than about 4, or greater than about 5. (Regardless of the ranges chosen, for a given ADF assembly 13, the Shade Number of the shutter in the intermediate state will always be higher than that of the shutter in the light state and lower than that of the shutter in the dark state). In a particular embodiment, the ADF assembly 13 can further include a detector which can be disabled or turned off when the ADF is placed in the grinding mode.

According to a further embodiment, when the helmet/ADF is placed in the grinding mode, for use, e.g., with an angle grinder, the ADF can be placed in the lightest state possible. Alternatively, when the helmet/ADF is placed in another mode of operation, for use, e.g., with a cutting torch, the ADF can be placed in an intermediate or dark state (by Shade Number) when a higher degree of protective shade is needed.

Figure 2:
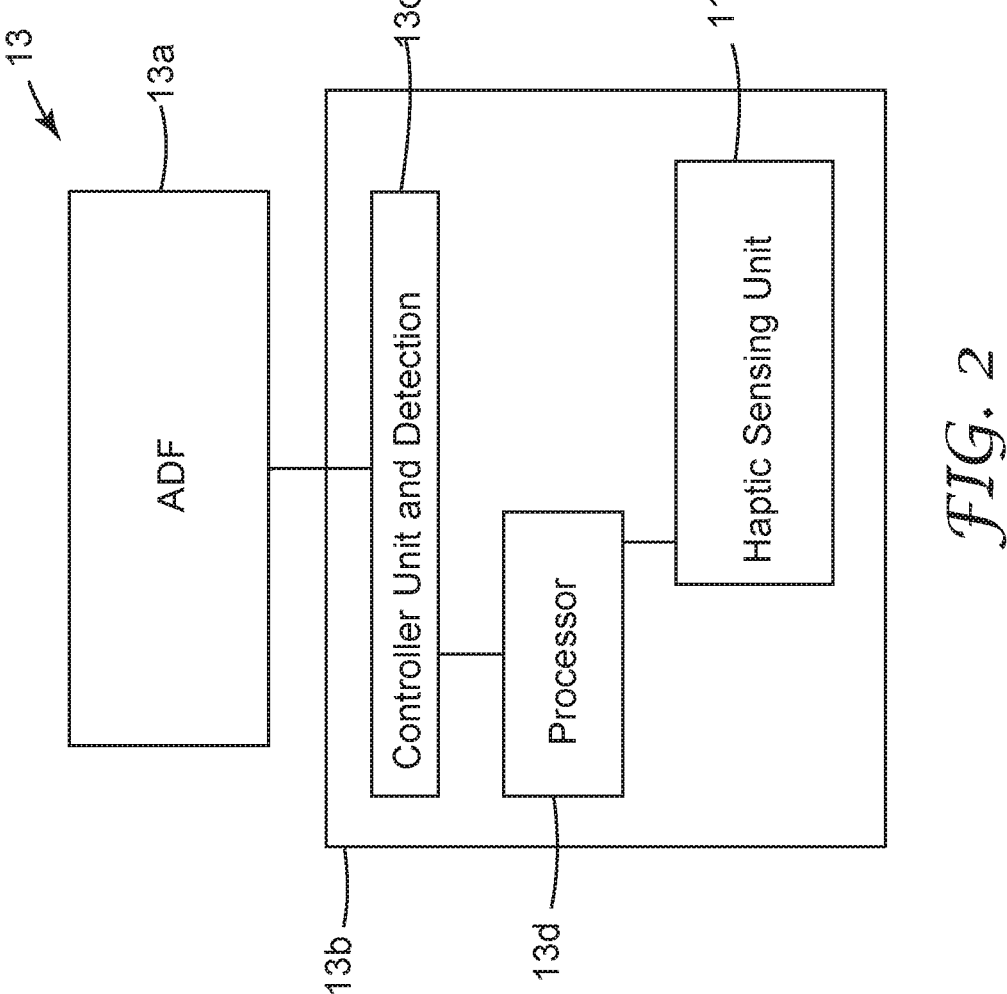
FIG. 2 is a schematic view of an ADF assembly in accordance with embodiments of the present invention.

FIG. 2 provides a schematic view of portions of the automatic darkening filter assembly 13 shown in FIGS. 1A and 1B. The ADF assembly 13 can include a filter portion 13a and controller electronics 13b. The controller electronics 13b can include a controller and detection unit 13c and a processor 13d. These components control filter operation and detect the presence of intense welding light. In addition, in accordance with embodiments of the invention, the haptic sensing unit 11 can also be disposed on the controller electronics 13b of the ADF assembly 13.

Figure 3:
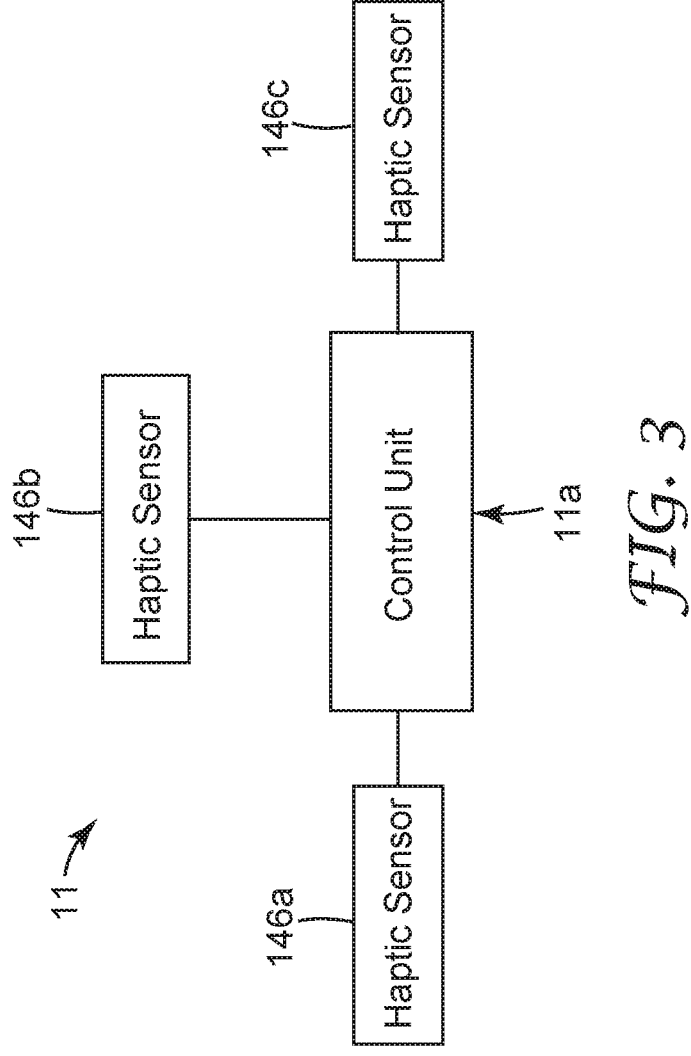
FIG. 3 is a schematic view of a haptic sensing unit in accordance with embodiments of the present invention.

The haptic sensing unit 11 can comprise a control unit 11a and one or more haptic sensors, e.g., haptic sensors 146a-146c as shown in FIG. 3, that can be disposed at one or more locations within welding protection device or welding helmet 10. Each haptic sensor can detect a touch pattern, such as a single or multiple touch, at a particular location on the welding protection device 10, such as the shield portion 12 and/or the ADF assembly 13, or other portions of the welding protection device 10. In accordance with yet another aspect of the invention, for a haptic sensor deployed to sense touch pattern on the ADF assembly 13, one or more sensors can be deployed to sense and differentiate between touch patterns made on different areas of the ADF assembly 13—for example, the centerline, the ADF assembly right side, the ADF assembly left side, the ADF assembly top region, and/or the ADF assembly bottom region. In addition, the one or more haptic sensors can be configured to distinguish between a touch pattern present on the ADF assembly 13 versus a touch pattern present on another portion of the welding protection device 10.

An exemplary haptic sensor may comprise a transducer (e.g., a surface acoustic wave sensor), an accelerometer, an infrared sensor, and/or a resistive or capacitive touch sensor.

In one embodiment, the haptic sensing unit 11 can further have software stored internally in, for example, memory.

In some aspects, the one or more sensors can be coupled via hard-wire or wirelessly coupled to the haptic sensing unit 11. In another example, a haptic sensor can comprise an accelerometer disposed within another portion of the welding protection device 10, e.g., the control circuit of the ADF assembly, so that a specific touch pattern placed on a particular region or multiple regions of the helmet/shield can be sensed by the accelerometer. Alternatively, the haptic sensing unit 11 can comprise a haptic sensor disposed at another location, such as the lateral side of the helmet.

According to an embodiment of the present invention, the haptic sensor unit 11 is programmed to execute a user-definable command. For example, if a particular touch pattern is sensed, the haptic sensor unit is configured to execute a particular command based on the particular touch pattern sensed. As noted above, a touch pattern may comprise a single touch, a multiple touch (e.g., a rapid two-touch or three-touch pattern, etc.), or a series of single or multiple touches within a particular time period, or a type of touch, such as a light tap or a hard tap. As such, the haptic sensor unit 11 can be programmed to execute multiple different commands based on any number of different touch patterns sensed. The user-definable command can comprise one or more individual commands. Alternatively, the command can comprise one or more toggling commands.

For example, the user-definable command can be one or more of the following commands: grinding mode on/off, locked dark state on/off, Feature on/off; Accessory (on/off/control), shade level higher/lower, sensitivity level higher/lower, and predefined user-mode toggle.

FIG. 1B shows the welding protection device 10 in an exploded view. It is noted that the exploded view is a type of illustration only and that certain components that appear to be spaced from each other are normally mounted in contact to each other as shown in FIG. 1A. The automatic darkening filter assembly 13 is mounted in a window 4 of the protective shield portion 12. Further, the welding protection device 10 can include a welding-arc-facing protective cover and an eye-facing protective cover. These protective covers prevent dust and splashes of molten or hot material from directly reaching the automatic darkening filter assembly 13 and thus provide for protecting the automatic darkening filter assembly 13 from damages. These protective covers may be exchangeable. Therefore, any damages from dust or splashes of molten or hot material may occur on the protective covers which are typically less expensive than the automatic darkening filter assembly 3. The welding protection device 10 in the example further has a front cover frame 21 for closing any gaps between the protective shield 12 and the cover frame and/or the automatic darkening filter assembly 13. In the example, the welding protection device 10 further has a headband arrangement 8 for fixing the welding protection device 10 on the welder's head.

In more detail, the automatic darkening filter assembly 13 can include a switchable light filter 13a. The switchable light filter can include one or more liquid crystal cells. For example, although not illustrated in detail, the switchable light filter 13a can include two liquid crystal cells (as mentioned above). In this embodiment, each liquid crystal cell has two transparent substrates, such as glass substrates. Each transparent substrate comprises a transparent electrode layer, in particular an indium tin oxide (ITO) layer, disposed on the transparent substrate, and an alignment layer disposed on the electrode layer. Between the transparent substrates a liquid crystal is disposed in direct contact with the alignment layers of the transparent substrates. On each transparent substrate a polarizer is disposed at the side opposite of the electrode and alignment layer. The alignment layers are arranged to orient the liquid crystal molecules in a determined direction when no voltage is applied to the electrode layers. Further, the polarizers are arranged such that in absence of the voltage light can pass through the liquid crystal cell. The second liquid crystal cell (of the same type as described) is arranged with one side on one of the polarizers and carries a third polarizer on the opposite side. Thus, the switchable light filter 13a has two liquid crystal cells and three polarizers. The third polarizer is arranged such that light can pass through the switchable light filter 13a in absence of a voltage applied to the electrode layers of the liquid crystal cells. Typically the switchable light filter 13a has at least one further permanent (not switchable) light filter, for example a UV light filter. The automatic darkening filter assembly 13 can have a flat or curved configuration and can include two flat or curved two liquid crystal cells.

The automatic darkening filter assembly 13 can further include control electronics 13b disposed on a printed circuit board and electronic circuitry (including light sensors) for switching the switchable light filter 13a. The printed circuit board can include controls, for example, push buttons, by which the automatic darkening filter assembly can be operated and configured by a user. For example, the automatic darkening filter assembly 13 comprises a button for activating the automatic switching between the dark-state and the light-state. Another button can control the sensitivity of the light sensors. Other buttons may be provided, for example one or more buttons for adjusting the light transmission level in the dark state. In this regard it is noted that in the dark-state the light transmission through the automatic darkening filter 13a is reduced only (and not entirely blocked) so that a welder can observe a welding arc but at (significantly) reduced brightness. The adjustment of the light transmission level in the dark state allows an adaptation to welding arcs of different light intensities, for example due to different welding techniques or welding applications. Thus, the welding protector can be used for a variety of different welding techniques and applications, including autogenous welding. In these alternative embodiments, the buttons can be utilized to access functions or modes in addition to those accessed via the aforementioned haptic controls.

Furthermore, the automatic darkening filter assembly 13 can include a housing having one or more parts that can be mounted to form a frame for holding the switchable light filter 13a. The housing can further provide a space for receiving the printed circuit board and a power supply, for example a battery.

The automatic darkening filter assembly 13 in the example further can include a receptacle or inserts for a battery or batteries.

The automatic darkening filter assembly 13 in the example may further include labels for marking any controls (for example push buttons) for operating the ADF assembly 13. Further, the labels may have instructions for a user, for example, instruction about an adjustment of the light transmission level in the dark-state for particular welding applications.

The automatic darkening filter assembly 13 forms a self-contained assembly unit which can be used in different welding protectors, such as a welding helmet or a welding shield, for example.

Figure 4:
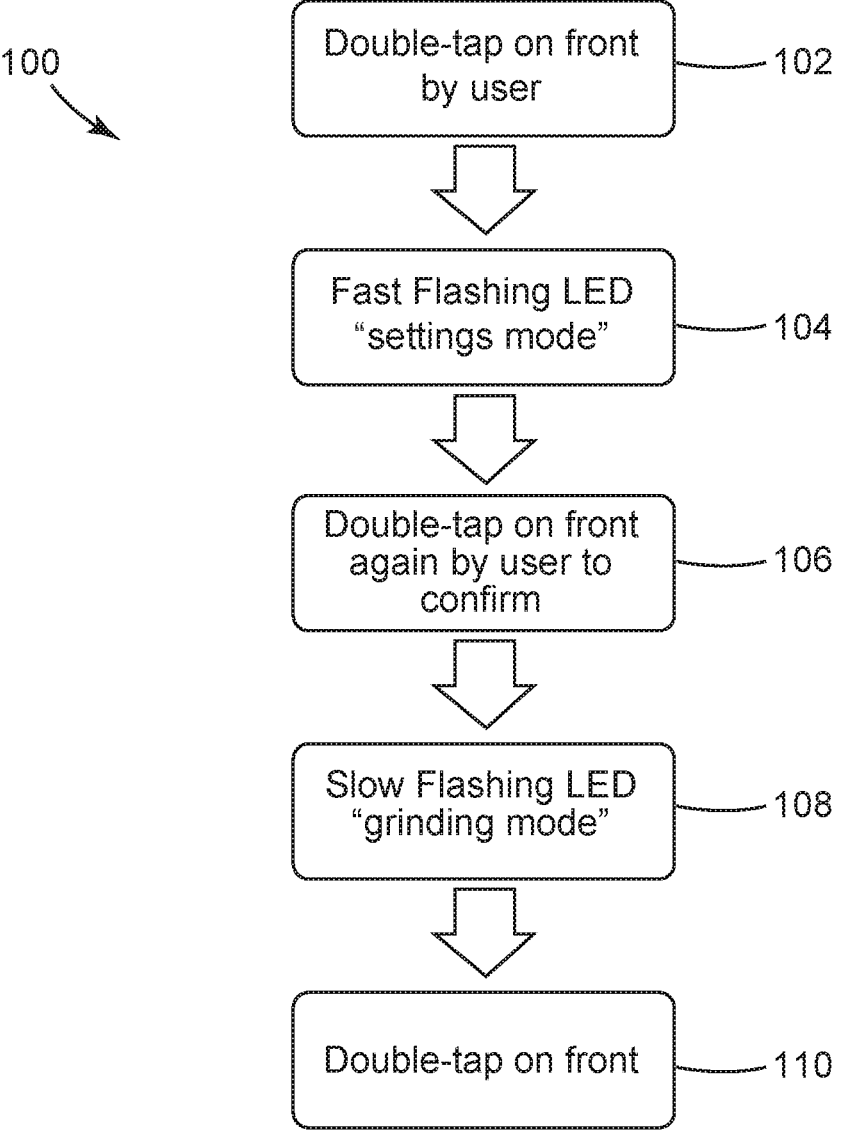
FIG. 4 is a flowchart of a process to change the operational state of a welding protection device in accordance with embodiments of the present invention.

When in use, the ADF assembly 13 is configured to provide a heads-up display for the wearer, providing the ability for wearer to change modes and welding operations via different haptic touch patterns, through push buttons, or a combination thereof. In one embodiment, as shown in FIG. 4, a touch pattern method 100 can be used to activate the grinding mode of the welding helmet 10 worn by a user/wearer. In step 102, a user/wearer initiates the process by making a double tap on the outer front portion of the ADF assembly 13. This double tap pattern initiates an indicator, such as a fast flashing LED, that is visible to the wearer in step 104, activating a "settings mode" state for the ADF assembly 13. In step 106, the user double taps the outer front portion of the ADF assembly 13 again to confirm. In step 108, the indicator provides a different signal, such as a slowly flashing LED which indicates that the "grinding mode" is engaged. As noted above, the "grinding mode" can place the ADF assembly 13 in a light state or an intermediate state, and lock the ADF assembly filter in that state for the duration of the grinding operation performed by the user/wearer. In step 110, the user/wearer can double tap the outer front portion of the ADF assembly 13 to exit the "grinding mode."

As would be apparent to one of skill in the art given the present description, alternative methods having different touch patterns, different welding functions, or combinations thereof can be also be implemented with the welding protection device 10. In addition, the haptic sensors of the haptic sensing unit 11 can be disposed at different locations of the helmet device 10, so that the user/wearer can activate the grinding or other operational mode by contacting that portion of the welding helmet 10 with the appropriate touch pattern.

Thus, embodiments of the present invention provide a welding protection device that comprises a haptic sensing unit that is configured to sense touch patterns. These touch patterns provide an efficient and rapid way for a user wearing the welding protection device to access various features of the welding protection device in a straightforward manner and without having to remove PPE, such as gloves.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, the welding protection device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope of the invention, which is limited only by the following claims.

What is claimed is:

1. A welding protection device, comprising:

a shield body;

an automatic darkening filter assembly insertable within the shield body and configured to enter into one or more different functional states, the automatic darkening filter assembly comprising a user interface that is inside the welding protection device when the automatic darkening filter assembly is inserted within the shield body; and a haptic sensing unit disposed within the welding protection device and configured to sense a touch pattern occurring on at least a first portion of the shield body or automatic darkening filter assembly such that a welder can tap anywhere on the first portion to switch functional states without the need for the welder to access and activate an external button on the welding protection device or the user interface inside the welding protection device.

2. The welding protection device of claim 1, wherein the haptic sensing unit comprises at least one haptic sensor.

3. The welding protection device of claim 2, wherein the at least one haptic sensor comprises at least one of an accelerometer, a transducer, and a touch sensor.

4. The welding protection device of claim 1, wherein the haptic sensor unit is programmed to execute a user-definable command.

5. The welding protection device of claim 4, wherein the user definable command includes one or more of the following commands: grinding mode on/off, locked dark state on/off, Feature on/off; Accessory (on/off/control), shade level higher/lower, sensitivity level higher/lower, and predefined user-mode toggle.

6. The welding protection device of claim 1, wherein the haptic sensor unit comprises a plurality of haptic sensors, wherein each sensor is disposed in a different portion of the shield portion or automatic darkening filter assembly.

7. The welding protection device of claim 1, wherein a first sensing unit comprises a first haptic sensor that senses a touch pattern performed on the automatic darkening filter assembly and a second haptic sensor that senses a touch pattern performed on the shield portion.

8. The welding protection device of claim 1, wherein the touch pattern includes a first double touch.

9. The welding protection device of claim 8, wherein the touch pattern includes a second double touch.

10. The welding protection device of any of claim 1, wherein the automatic darkening filter assembly operates in a light-state mode when the haptic sensor senses a predetermined touch pattern.

11. The welding protection device of claim 1, wherein the automatic darkening filter assembly operates in an intermediate-state mode when the haptic sensor senses a predetermined touch pattern.

12. The welding protection device of claim 1, wherein a first haptic sensor is mounted within a first portion of the automatic darkening filter assembly.

13. The welding protection device of claim 1, wherein a first haptic sensor is configured to distinguish between a first touch pattern executed on a first portion of the automatic darkening filter assembly and a second touch pattern executed on a second portion of the automatic darkening filter assembly.

14. The welding protection device of claim 1, wherein a first haptic sensor is mounted within the shield body.

15. A method of entering into a grinding mode for a welding protection device having a shield body and an automatic darkening filter assembly comprising a user interface that is inside the welding protection device when the automatic darkening filter assembly is inserted within the shield body, comprising:

providing a haptic sensing unit within the welding protection device having a haptic sensor configured to sense a touch pattern occurring on at least a first portion of the shield body or automatic darkening filter assembly such that a welder can tap anywhere on the first portion to switch functional states without the need for the welder to access and activate an external button on the welding protection device or the user interface inside the welding protection device;

executing a user definable command when the haptic sensor senses a touch pattern occurring anywhere on at least a first portion of shield body or automatic darkening filter assembly; and triggering a particular light state for the automatic darkening filter assembly based on the touch pattern sensed.

16. The method of claim 15, wherein the user definable command includes one or more of the following commands: grinding mode on/off, locked dark state on/off, Feature on/off; Accessory (on/off/control), shade level higher/lower, sensitivity level higher/lower, and predefined user-mode toggle.

* * * * *